(12) United States Patent
Zhan et al.

(10) Patent No.: US 6,875,374 B1
(45) Date of Patent: Apr. 5, 2005

(54) CERAMIC MATERIALS REINFORCED WITH SINGLE-WALL CARBON NANOTUBES AS ELECTRICAL CONDUCTORS

(75) Inventors: Guodong Zhan, Davis, CA (US); Joshua D. Kuntz, Lafayette, CA (US); Amiya K. Mukherjee, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 15 days.

(21) Appl. No.: 10/377,137

(22) Filed: Feb. 26, 2003

(51) Int. Cl.[7] .......................... H01B 1/14; C04B 35/18; C04B 35/52
(52) U.S. Cl. ................ 252/502; 252/518.1; 423/445 B; 423/592.1; 501/95.2; 501/99; 501/100; 264/430; 977/DIG. 1
(58) Field of Search ............................. 252/502, 518.1; 501/95.2, 99, 100; 423/445 B, 592.1; 264/430; 977/DIG. 1

(56) References Cited

U.S. PATENT DOCUMENTS 6,420,293 B1 * 7/2002 Chang et al. ............... 501/95.2

OTHER PUBLICATIONS

Flahaut et al, "Carbon Nanotube–metal–oxide nanocomposites: Microstructure, Electrical Conductivity and Mechanical Properties," Acta. mater. 2000 (48) pp 3803–3812.*

Peigney et al, "Carbon Nanotubes in Novel Ceramic Matrix Nanocomposites," Ceramics International, 2000, (26) 677–683.*

* cited by examiner

Primary Examiner—Mark Kopec
Assistant Examiner—Kallambella Vijayakumar
(74) Attorney, Agent, or Firm—M. Henry Heines; Townsend and Townsend and Crew, LLP

(57) ABSTRACT

Composite materials formed of a matrix of fused ceramic grains with single-wall carbon nanotubes dispersed throughout the matrix and a high relative density, notably that achieved by electric field-assisted sintering, demonstrate unusually high electrical conductivity in combination with high-performance mechanical properties including high fracture toughness. This combination of electrical and mechanical properties makes these composites useful as electrical conductors in applications where high-performance materials are needed due to exposure to extreme conditions such as high temperatures and mechanical stresses.

13 Claims, 1 Drawing Sheet

CERAMIC MATERIALS REINFORCED WITH SINGLE-WALL CARBON NANOTUBES AS ELECTRICAL CONDUCTORS

STATEMENT AS TO RIGHTS TO INVENTIONS MADE UNDER FEDERALLY SPONSORED RESEARCH OR DEVELOPMENT

This invention was made with Government under Contract No. G-DAAD 19-00-1-0185, awarded by the United States Army Research Office. The Government has certain rights in this invention.

BACKGROUND OF THE INVENTION

1. Field of the Invention

This invention resides in the field of electrically conductive ceramics, and incorporates technologies relating to nanocrystalline materials, carbon nanotubes, and sintering methods for densification and property enhancement of materials.

2. Description of the Prior Art

The ability of ceramics to withstand extreme conditions of temperature, mechanical stress, and chemical exposure without failure or with a very low failure rate has led to the use of ceramics in applications that require high-performance materials, such as heat engines, cutting tools, wear and friction surfaces, and space vehicles. In recent years, the use of ceramics has extended into the fields of microtechnology and nanotechnology, since the increasing demands of nano-scale electronics and microelectromechanical systems (MEMS) for example have prompted researchers to investigate the use of ceramics in these areas as well.

An unfortunate characteristic of nanocrystalline ceramics is brittleness. To reduce the brittleness, composites have been developed in which secondary materials are dispersed throughout the ceramic matrix. In some of the more recent developments, carbon nanotubes, specifically multi-wall carbon nanotubes, have been used as the secondary material. A description of "ceramic matrix nanocomposites containing carbon nanotubes" is found in Chang, S., et al. (Rensselaer Polytechnic Institute), U.S. Pat. No. 6,420,293 B1, issued Jul. 16, 2002 on an application filed on Aug. 25, 2000. While the description encompasses both single-wall and multi-wall carbon nanotubes, the only carbon nanotubes for which test data is presented in the patent are multi-wall carbon nanotubes. To form the composites, the starting powders in the patent are sintered into a dense continuous mass by hot isostatic pressing. Single-wall carbon nanotubes, although not investigated to the extent of multi-wall carbon nanotubes for this purpose, are known to have both high stiffness (a Young's modulus of 1,400 GPa) and high strength (a tensile strength well above 100 GPa).

In addition to applications where their mechanical properties are needed, ceramics are of increasing interest in electronics since various kinds of electrical devices are being designed for use in environments that require a combination of high temperature resistance, toughness, and chemical inertness. In the microelectronics industry, for example, materials with the qualities demonstrated by ceramics are sought for use as silicon substitutes, as trays and wafer carriers, as ruggedized microchip substrates, and as components with electrostatic discharge protection. In the microwave industry, the high-temperature environments that are frequently encountered require high-performance materials that can shield components from, or absorb, electromagnetic interference. In the automotive industry, high-temperature, high-strength, chemically inert materials that conduct electricity are needed for components such as fuel injector assemblies. The need for these qualities extends to medicine as well, where a wide variety of medical devices, such as implants, prostheses, and surgical devices, would benefit from a combination of electrical functionality, high strength and chemical inertness. In electrical power supplies such as batteries and solid oxide fuel cells, electrodes that possess these properties are needed. The need also exists in analytical and testing devices for materials used as chemical sensors, gas separation materials, and materials for hydrogen absorption. And in the aerospace and defense industries, materials with these properties are needed for aircraft and aircraft engines as well as for thermal management materials in human spaceflight applications.

Ceramics are electrically insulating materials. To make them electrically conductive, ceramics have been formulated as composites with electrically conductive fillers. Carbon nanotubes have been investigated as conductive fillers since carbon nanotubes are known to possess both high electrical conductivity and high thermal conductivity. Studies of the electrical characteristics of ceramic composites that contain carbon nanotubes, notably composites of alumina, iron and carbon nanotubes, composites of magnesium oxide, cobalt and carbon nanotubes, and composites of $MgAl_2O_4$, iron, cobalt, and carbon nanotubes have been reported by Flahaut, E., et al., "Carbon Nanotubes-Metal-Oxide Nanocomposites: Microstructure, Electrical Conductivity, and Mechanical Properties," *Acta Mater.* 48: 3803–3812 (2000); Laurent, Ch., et al., "Carbon Nanotubes-Fe-Alumina Nanocomposites. Part II: Microstructure and Mechanical Properties of the Hot-Pressed Composites," *J. Euro. Ceram. Soc.* 18: 2005–2013 (1998); Peigney, A., et al., "Carbon Nanotubes-Fe-Alumina Nanocomposites. Part I: Influence of the Fe Content on the Synthesis of Powders," *J. Euro. Ceram. Soc.* 18: 1995–2004 (1998); Peigney, A., et al., "Carbon Nanotubes in Novel Ceramic Matrix Nanocomposites," *Ceram. Inter.* 26: 677–683 (2000); Peigney, A., et al., "Carbon Nanotubes Grown in-situ by a Novel Catalytic Method," *J. Mater. Res.* 12: 613–615 (1997); Peigney, A., et al., "Aligned carbon nanotubes in ceramic-matrix nanocomposites prepared by high-temperature extrusion," *Chem. Phys. Lett.* 352: 20–25 (2002). The nanocomposites in these reports were produced by hot pressing nano-sized powders. The composites were electrically conductive to a moderate degree with an electrical conductivity within the range of 0.2–4.0 S/cm. The fracture strengths and fracture toughnesses of the composites were generally lower however than those of the metal-ceramic composites (lacking carbon) and only marginally higher than those of the pure ceramics. The Peigney et al. 2002 paper (*Chem. Phys. Lett.* 352: 20–25 (2002)) also reports that the carbon nanotubes in the composites can be aligned in the bulk ceramic matrix of the composite by a high-temperature extrusion technique to produce materials that show an anisotropy of electrical conductivity. The best conductivity however was only obtainable in the center of the extrusion since the carbon nanotubes in other parts of the composite had been damaged during the extrusion.

Of further relevance to this invention is the literature on electric field-assisted sintering, which is also known as spark plasma sintering, plasma-activated sintering, and field-assisted sintering technique. Electric field-assisted sintering is disclosed in the literature for use on metals and ceramics, for consolidating polymers, for joining metals, for crystal growth, and for promoting chemical reactions. The densification of alumina powder by electric field-assisted sintering is disclosed by Wang, S. W., et al., *J. Mater. Res.* 15(4) (April 2000): 982–987.

SUMMARY OF THE INVENTION

It has now been discovered that a composite material formed of a matrix of fused ceramic grains with single-wall carbon nanotubes dispersed throughout the matrix and a high relative density demonstrates unusually high electrical conductivity in combination with favorable mechanical properties including a high fracture toughness. The density is within the range of density that is achievable by electric field-assisted sintering, which is a preferred method of densification. This invention thus resides in electrical devices, electrical systems, and electrical applications in general in which a composite of this description is interposed between two terminals between which a voltage has been applied to provide an electrical conduction path and to thereby serve as an electrical conducting medium between the terminals. The electrical conductivity of the composite far exceeds the electrical conductivities of composites of similar composition but with lower relative densities that are typically achieved by means other than electric field-assisted sintering. The electrical conductivity of the composite also far exceeds that of composites with lower relative densities that contain conductive metals dispersed throughout the ceramic matrix in addition to the carbon nanotubes. The invention thus finds application in each of the various electrical systems and applications listed above.

In the preferred embodiments of the invention that achieve densification by electric field-assisted sintering, the invention offers the further advantage of a reduction in processing time due to the speed with which electric field-assisted sintering can be performed relative to other sintering methods.

These and other features, advantages and objects of this invention will be apparent from the description that follows. All literature references cited in this specification are incorporated herein by reference for their descriptions of the subject matter that is addressed in the contexts in which the citations are made.

DETAILED DESCRIPTION OF THE INVENTION AND PREFERRED EMBODIMENTS

Figure 1:
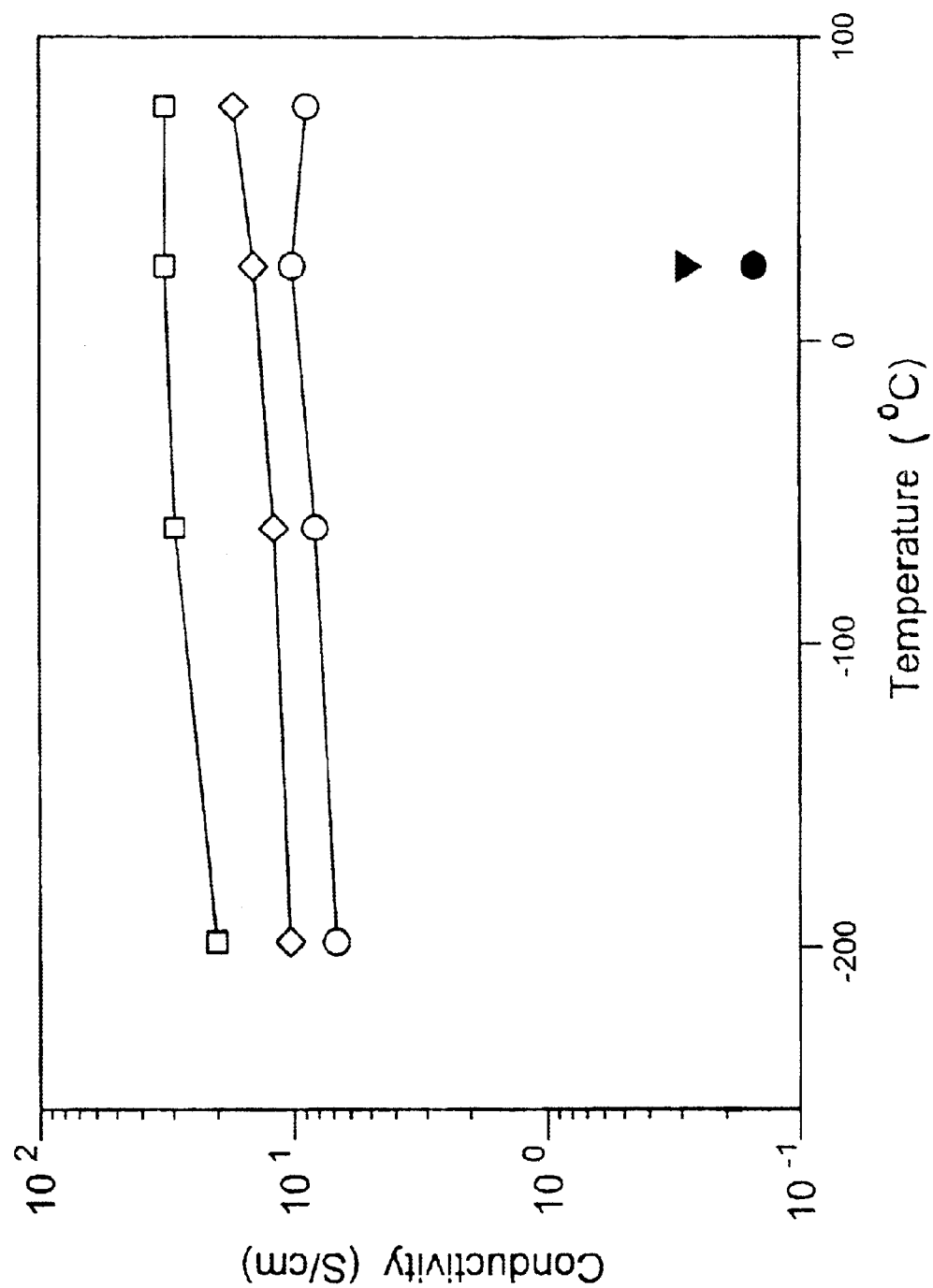
FIG. 1 is a plot of the electrical conductivity of certain composites of alumina and carbon nanotubes vs. temperature, listing test results generated by the inventors herein together with test results reported in the literature.

The ceramic materials that form the major component of the composites of this invention include any known ceramics, although preferred ceramics for use in this invention are metal oxides. Examples of metal oxide ceramics are alumina, magnesium oxide, titania, cerium oxide, yttria, and zirconia. Further examples are combinations of two or more of these metal oxides, and combinations that include other oxides such as silica and other metal and non-metal oxides. Still further examples are mixed metallic oxides such as SiAlON, AlON, spinels such as magnesia spinel, and calcium aluminate. A metal oxide that is currently of particular interest is alumina, either α-alumina, γ-alumina, or a mixture of both.

Carbon nanotubes are polymers of pure carbon. Both single-wall and multi-wall carbon nanotubes are known in the art and the subject of a considerable body of published literature. Examples of literature on the subject are Dresselhaus, M. S., et al., *Science of Fullerenes and Carbon Nanotubes*, Academic Press, San Diego (1996), and Ajayan, P. M., et al., "Nanometre-Size Tubes of Carbon," *Rep. Prog. Phys.* 60(1997): 1025–1062. The structure of a single-wall carbon nanotube can be described as a single graphene sheet rolled into a seamless cylinder whose ends are either open or closed. When closed, the ends are capped either by half fullerenes or by more complex structures such as pentagonal lattices. The average diameter of a single-wall carbon nanotube is within the range of 0.5 to 100 nm, and more typically, 0.5 to 10 nm, 0.5 to 5 nm, or 0.7 to 2 nm. The aspect ratio, i.e., length to diameter, can range from about 25 to about 1,000,000, and preferably from about 100 to about 1,000. Thus, a nanotube of 1 nm diameter may have a preferred length of from about 100 to about 1,000 nm. (All ranges stated herein are approximate.) Nanotubes frequently exist as "ropes," which are bundles of 10 to 500 single-wall nanotubes held together along their lengths by van der Waals forces. Individual nanotubes often branch off from a rope to join nanotubes of other ropes. Multi-walled carbon nanotubes are two or more concentric cylinders of graphene sheets. The cylinders are of successively larger diameter to fit one inside another, forming a layered composite tube bonded together by van der Waals forces, the distance between layers typically being approximately 0.34 nm as reported by Peigney, A., et al., "Carbon nanotubes in novel ceramic matrix nanocomposites," *Ceram. Inter.* 26 (2000) 677–683.

Carbon nanotubes are commonly prepared by are discharge between carbon electrodes in an inert gas atmosphere. The product is generally a mixture of single-wall and multi-wall nanotubes, although the formation of single-wall nanotubes can be favored by the use of transition metal catalysts such as iron or cobalt. Single-wall nanotubes can also be prepared by laser ablation, as disclosed by Thess, A., et al., "Crystalline Ropes of Metallic Carbon Nanotubes," *Science* 273 (1996): 483–487, and by Witanachi, S., et al., "Role of Temporal Delay in Dual-Laser Ablated Plumes," *J. Vac. Sci. Technol. A* 3 (1995): 1171–1174. A further method of producing single-wall nanotubes is the HiPco process disclosed by Nikolaev, P., et al., "Gas-phase catalytic growth of single-walled carbon nanotubes from carbon monoxide," *Chem. Phys. Lett.* 313, 91–97 (1999), and by Bronikowski M. J., et al., "Gas-phase production of carbon single-walled nanotubes from carbon monoxide via the HiPco process: A parametric study," *J. Vac. Sci. Technol.* 19, 1800–1805 (2001).

The composites of this invention can further include conductive metals such as iron, aluminum or copper, dispersed throughout the composite to further enhance the electrical conductivity of the composite. In certain preferred embodiments of the invention, however, such metals are not included, and the composite consists entirely of a ceramic matrix with carbon nanotubes dispersed throughout the matrix as the sole non-ceramic component.

The starting materials for the composites of this invention are preferably powder mixtures of the ceramic material and the single-wall carbon nanotubes. The composites of this invention may contain multi-wall carbon nanotubes in addition to the single-wall carbon nanotubes. It is preferred however that the mixtures, and the final product as well, be free of multi-wall carbon nanotubes, or if multi-wall carbon nanotubes are present, that their amounts relative to the amount of single-wall nanotubes be so small that the presence of the double-wall or multi-wall nanotubes does not obliterate or significantly reduce the beneficial properties attributable to the single-wall nanotubes.

The relative amounts of ceramic material and single-wall carbon nanotubes can vary, although the mechanical properties and possibly the performance characteristics may vary with the proportions of the single-wall carbon nanotubes. In most cases, best results will be achieved with composites in which the single-wall carbon nanotubes constitute from about 1% to about 50%, preferably from about 5% to about 25%, and most preferably from about 5% to about 20%, by volume of the composite. The volumes used in determining the volume percents referred to herein are calculated from the weight percents of the bulk starting materials and the theoretical density of each component.

The ceramic material used as a starting material is preferably in the form of particles in the micro- or nano-size range, particularly particles that are less than 500 nm in diameter on the average. The carbon nanotubes can be dispersed through the ceramic powder by conventional means to form a homogeneously dispersed powder mixture, although a preferred method is one in which the materials are mixed by being suspended together in a common liquid suspending medium. Any readily removable, low viscosity, inert suspending liquid, such as a low molecular weight alcohol (ethanol, for example), can be used. Carbon nanotubes are available from commercial suppliers in a paper-like form, and can be dispersed in ethanol and other liquid suspending agents with the assistance of ultrasound.

Once the ceramic powder and carbon nanotubes are combined, the powders are preferably mixed prior to electric field-assisted sintering. Mixing can be done on the powders alone or on a suspension of the powders. Mechanical mixing can be performed by ball-milling in conventional rotary mills that mix the powder mixture with the assistance of tumbling balls. The sizes of the balls, the number of balls used per unit volume of powder, the rotation speed of the mill, the temperature at which the milling is performed, and the length of time that milling is continued can all vary widely. Best results will generally be achieved with a milling time ranging from about 4 hours to about 50 hours. The degree of mixing may also be affected by the "charge ratio," which is the ratio of the mass of the balls to the mass of the powder. A charge ratio of from about 5 to about 20 will generally provide proper mixing.

The consolidation of the product can be enhanced by mechanical activation of the ceramic particles prior to consolidating them into the composite. Mechanical activation can be achieved by high-energy ball milling utilizing ball mills as described in the preceding paragraph but at an increased intensity and for an extended period of time. Included among the beneficial effects of high-energy ball milling are a reduction in particle size.

The composite materials can be consolidated into a continuous mass by conventional means of compression. The benefits of the invention will be most evident when the composite is densified to a high density, i.e., one that approaches full theoretical density, which is the density of the material as determined by volume-averaging the densities of each of its components. A density of at least 95% of the theoretical density is sought, preferably at least 98%, and most preferably at least 99%. The term "relative density" is used herein to denote the actual density expressed as a percent of the theoretical density.

The preferred method of densification is electric field-assisted sintering. One method of performing this type of sintering is by passing a pulsewise DC electric current through the dry powder mixture or through a consolidated mass of the mixture while applying pressure. A description of electric field-assisted sintering and of apparatus in which this process can be performed is presented by Wang, S. W., et al., "Densification of $Al_2O_3$ powder using spark plasma sintering," J. Mater. Res. 15(4), 982–987 (2000). While the conditions may vary, best results will generally be obtained with a densification pressure exceeding 10 MPa, preferably from about 10 MPa to about 200 MPa, and most preferably from about 40 MPa to about 100 MPa. The preferred current is a pulsed DC current of from about 250 $A/cm^2$ to about 10,000 $A/cm^2$, most preferably from about 500 $A/cm^2$ to about 1,500 $A/cm^2$. The duration of the pulsed current will generally range from about 1 minute to about 30 minutes, and preferably from about 1.5 minutes to about 5 minutes. Preferred temperatures are within the range of from about 800° C. to about 1,500° C., and most preferably from about 900° C. to about 1,400° C. Densification is typically performed by uniaxial compression under vacuum, and preferred vacuum levels for the densification are below 10 Torr, and most preferably below 1 Torr.

The prefix "nano-" as used herein generally refers to dimensions that are less than 100 mm. The ceramic powders used as starting materials in the practice of this invention are preferably in the nano-size range although powders with particle sizes above 100 nm can be used as well. In addition, the particles in many cases undergo grain growth during sintering. The resulting composites may therefore have grain sizes that exceed the nano-size range by several hundred nanometers.

The composites of this invention are useful as conducting media in any application requiring an electrical conduction path in a material that is capable of withstanding extreme conditions of temperature, mechanical stress, or both. The path can assume the form of a coating on an electrically insulating substrate, a lead joining components of an electrical circuit or system of circuits, a wire, a conductive line on printed circuit boards, and any other circuitry application in high-performance applications. The range of possibilities will be readily apparent to those skilled in the art.

The following examples are offered for purposes of illustration and are not intended to limit the scope of the invention.

EXAMPLES

Materials, Equipment, and Experimental Procedures

Purified single-wall carbon nanotubes produced by the HiPco process with more than 90% of the catalyst removed were obtained from Carbon Nanotechnologies Incorporated (Houston, Tex., USA). The nanotubes were in paper form, and once obtained were dispersed in ethanol with the assistance of ultrasound. The ceramic material was nanocrystalline alumina powder. A mixture consisting of 80% α-$Al_2O_3$ and 20% γ-$Al_2O_3$ with particle sizes of 300 nm (40 nm crystallite size) and 20 nm, respectively, was obtained from Baikowski International Corporation (Charlotte, N.C., USA). In addition, γ-$Al_2O_3$ with average particle sizes of 15 nm and 32 nm and synthesized by gas condensation was obtained from Nanophase Technologies Corporation (Darien, Ill., USA).

For certain experiments, the alumina or alumina mixture was first mechanically activated by high-energy ball milling prior to being combined with the carbon nanotubes. The high-energy ball milling was performed on a Spex 8000 mixer mill (Spex Industries, Metuchen, N.J., USA) in a zirconia vial with 1 weight percent polyvinyl alcohol, a dry milling agent, to prevent severe powder agglomeration.

Milling was performed at room temperature for 24 hours, followed by vacuum heat treatment at 350° C. for 3 hours to remove the polyvinyl alcohol. Thus milled, the alumina was mixed with the single-wall carbon nanotube dispersion, and the combined dispersion was sieved using a 200-mesh sieve, then ball-milled for 24 hours (still in ethanol) using zirconia milling media, then dried to form a dry powder mixture.

All dry powder samples, including those containing alumina mechanically activated by high-energy ball milling and those containing alumina that had not been activated, were placed on a graphite die of inner diameter 20 mm and cold-pressed at 200 MPa. The cold-pressed powder mixture was then sintered on a Dr. Sinter 1050 Spark Plasma Sintering System (Sumitomo Coal Mining Company, Japan) under vacuum. Electric field-assisted sintering was then performed at an applied pressure of 80 MPa with a pulsed DC current of 5,000 A maximum and a maximum voltage of 10 V. The pulses were 12 ms in duration separated by intervals of 2 ms. Once the pressure was applied, the samples were heated to 600° C. in 2 minutes and then heated further at rates of 550° C./min to 600° C./min to 1,150–1200° C. where they were held for 3 minutes. The temperature was monitored with an optical pyrometer focused on a depression in the graphite die measuring 2 mm in diameter and 5 mm in depth.

The final densities of the sintered compacts were measured by the Archimedes method using deionized water as the immersion medium. The density of the single-wall carbon nanotubes used as a starting material was 1.8 g/cm$^3$. Microstructure determinations of the sintered compacts were performed with an FEI XL30-SFEG high-resolution scanning electron microscope with a resolution better than 2 nm. Grain sizes were estimated by high-resolution scanning electron microscopy of fracture surfaces and x-ray diffraction profiles. Additional characterization by analytical electron microscopy and high-resolution transmission electron microscopy was performed on a Philips CM-200 with a field emission gun operating at 200 kV. Indentation tests were performed on a Wilson Tukon hardness tester with a diamond Vickers indenter. Bulk specimens were sectioned and mounted in epoxy, then polished through 0.25-micron diamond paste. The indentation parameters for fracture toughness ($K_{IC}$) were a 2.5 kg load with a dwell time of 15 seconds. The fracture toughness was calculated by the Anstis equation as disclosed by Anstis, G. R., et al., "A Critical Evaluation of Indentation Techniques for Measuring Fracture Toughness: I, Direct Crack Measurement," *J. Am. Ceram. Soc.* 64(9): 533–538 (1981). At least ten measurements were performed for each sample.

An Agilent 34420A nano Volt/microOhm meter (Agilent Technologies, Palo Alto, Calif., USA) was used for conductivity measurement using a four-wire probe technique. To remove the effect of extraneous voltages such as those arising due to thermal EMF caused by dissimilar materials in the circuit, two measurements were made for every reading: one with the current on and the other with the current off. Using this configuration the meter has a resolution of 0.1 $\mu\Omega$. The four-point probe electrical conductivity ($\sigma$) of the dense materials was measured at four different temperatures: −196° C., −61° C., 25° C., and 77° C.

A composite prepared from 15-nm γ-alumina particles that had been activated by high-energy ball milling and 15 volume percent single-wall carbon nanotubes was prepared by the procedure described above. The same procedure was used to prepare a composite starting with 32-nm γ-alumina particles that had not been activated by high-energy ball milling and 10 volume percent single-wall carbon nanotubes, and another composite starting with an alumina mixture consisting of 80% 300-nm α-alumina and 20% 20-nm γ-alumina, also without activation by high-energy ball milling, and 5.7 volume percent single-wall carbon nanotubes. The procedure was also performed on pure alumina (a mixture consisting of 80% 300-nm α-alumina and 20% 20-nm γ-alumina), also without activation by high-energy ball milling. Since pure α-alumina nanopowders can be consolidated to full density by electric field-assisted sintering at 1,150° C. for three minutes, those specimens containing α-alumina were sintered under these conditions. By contrast, γ-alumina requires a sintering temperature of 1,200° C. to achieve full density, and accordingly the specimen containing γ-alumina was sintered at this higher temperature.

Results

The relative density, grain size, and specific conductivity were determined on the sintered alumina and the sintered samples of each of the three composites, and the results are listed in Table I, together with data for nanocomposites and other materials selected from the prior art as representative of the state of the art preceding this invention. For each entry, the table lists the composition, expressed in terms of the components of the composite (where "SWCN" denotes single-wall carbon nanotubes. "MWCN" denotes multi-wall carbon nanotubes," and "CNT" denotes carbon nanotubes that are unspecified as either single-wall or multi-wall), including the type and grain size of the starting alumina (where known), and the volume percent of each component; the processing conditions including high-energy ball milling ("HEBM") when used and the sintering method, expressed as either electric field-assisted sintering ("SPS" as an abbreviation for "spark plasma sintering"), hot pressing ("HP"-sintering in the absence of an electric field), or high-temperature extrusion ("HTE"); the grain size of the sintered product; the specific conductivity at 25° C.; and the source of the data, i.e., either the inventors herein or the literature citation (identified in the list following the table). Analysis of the alumina-containing products by x-ray diffraction after sintering revealed that the alumina in all of these products was exclusively α-alumina. To obtain the relative density, the theoretical density is first calculated as the total of the densities of the components multiplied by their volume percents, and the measured density is then expressed as a percent of the theoretical density.

TABLE I

Compositions, Processing Conditions, Relative Densities, Grain Size and Specific Conductivities ($\sigma$) of Composites Within the Scope of the Invention vs. Materials of the Prior Art

| No. | Composition - additive(s) and volume %; matrix in parentheses | Processing Conditions | Relative Density (%) | Grain Size (nm) | $\sigma$ (S/cm at 25° C.) | Source |
|---|---|---|---|---|---|---|
| (1) | 0% (pure $\alpha$-$Al_2O_3$) | SPS/1150° C./3 min | 100 | 349 | $10^{-12}$ to $10^{-14}$ | herein |
| (2) | SWCN: 5.7% ($\alpha$-$Al_2O_3$) | SPS/1150° C./3 min | 100 | ~200 | 10.50 | herein |
| (3) | SWCN: 10% ($\gamma$-$Al_2O_3$, 32 nm) | SPS/1200° C./3 min | 97.5 | ~100 | 15.11 | herein |
| (4) | SWCN: 15% ($\gamma$-$Al_2O_3$, 15 nm) | HEBM/SPS/ 1150° C./3 min | 99.2 | ~100 | 33.45 | herein |
| (5) | CNT: 8.5%; Fe: 4.3% ($\alpha$-$Al_2O_3$) | HP/1500° C./15 min | 88.7 | ~300 | 0.4–0.8 | (i) |
| (6) | CNT: 10%; Fe: 4.3% ($\alpha$-$Al_2O_3$) | HP/1500° C./15 min | 87.5 | ~300 | 2.8–4.0 | (i) |
| (7) | Aligned CNT: 10%; Fe: 4.3% ($\alpha$-$Al_2O_3$) | HTE/1500° C./15 min | 90 | 500 | 0.8–1.6 | (ii) |
| (8) | Aligned CNT: 9.8%; Fe/Co: 3.2% ($MgAl_2O_4$) | HTE/1500° C./15 min | 90 | 800 | 0.6–2.0 | (ii) |
| (9) | $\beta$"-$Al_2O_3$ ceramic ion conductor | — | — | — | ~0.25 | (iii) |
| (10) | MWCN: 20% (polymer) | — | — | — | ~0.3 | (iv) |
| (11) | 0% (aluminum) | — | — | — | 294.12 | (v) |
| (12) | CNT: 1 weight % (aluminum) | HP/520° C./30 min | — | — | 204.08 | (v) |
| (13) | CNT: 4 weight % (aluminum) | HP/520° C./30 min | — | — | 151.52 | (v) |
| (14) | CNT: 10 weight % (aluminum) | HP/520° C./30 min | — | — | 181.82 | (v) |

Literature sources:
(i) Flahaut, E., et al., "Carbon Nanotubes-Metal-Oxide Nanocomposites: Microstructure, Electrical conductivity, and Mechanical Properties," Acta Mater. 48: 3803–3812 (2000)
(ii) Peigney, A., et al., "Aligned carbon nanotubes in ceramic-matrix nanocomposites prepared by high-temperature extrusion," Chem. Phys. Lett. 352: 20–25 (2002)
(iii) Ceramic Innovations in the 20th Century, Wachtman, J. B., Jr., ed., pp. 152–154, published by the American Chemical Society (1999)
(iv) Yoshino, K., et al., "Electrical and optical properties of conducting polymer-fullerene and conducting polymer-carbon nanotube composites," Full. Sci. Technol. 7: 695–711 (1999)
(v) Xu, C. L., et al., "Fabrication of aluminum-carbon nanotube composites and their electrical properties," Carbon 37: 855–858 (1999)

The specimens represented by rows (2) through (4) of Table I are the only specimens among those in the Table that fall within the scope of the present invention. The data show that alumina, which is normally an electrical insulator with high electrical resistance, becomes electrically conductive when formed into composites that incorporate small amounts of single-wall carbon nanotubes and densified by electric field-assisted sintering, and that the electrical conductivity of such a composite increases with the carbon nanotube content. Thus the conductivity at room temperature of a composite containing 5.7 volume percent carbon nanotubes that has been sintered by electric field-assisted sintering is 10.50 S/cm (second row of data in the Table). At the 10% level, the composites of this invention (third row of data) exhibit more than three times the conductivity of the 10% carbon nanotube composite of the Flahaut et al. reference that has been sintered by means other than electric field-assisted sintering (sixth row of data), and by increasing the carbon nanotube level to 15% (fourth row of data) the result is more than eight times the conductivity of the 10% composite of the Flahaut et al. reference. This value (fourth row of data) is more than 100 times the value of the $\beta$"-alumina ceramic ion conductor (eighth row of data). This increase of conductivity with increasing carbon nanotube content is contrary to reports in the literature, which teaches that the conductivity decreases with carbon nanotube content rather than increasing in metal-matrix composites (Xu et al. 1999, source (v)).

The variation of electrical conductivity with temperature is shown in FIG. 1 for the three composites of Table I that are within the scope of the invention together with the values for other composites from the Table. The symbols used in FIG. 1 are as follows:

open squares: composite of the present invention with 15% single-wall carbon nanotubes, alumina pre-activated by high-energy ball milling, sintered by electric field-assisted sintering open diamonds: composite of the present invention with 10% single-wall carbon nanotubes without pre-activation of alumina, sintered by electric field-assisted sintering open circles: composite of the present invention with 5.7% single-wall carbon nanotubes without pre-activation of alumina, sintered by electric field-assisted sintering filled triangle (pointing upward): data generated by Flahaut et al. above, source (i), on composites containing 10% carbon nanotubes of unspecified type and 4.3% iron and in which sintering was performed by hot pressing at 1,500° C. for 15 minutes in the absence of an electric field filled inverted triangle (pointing downward): data generated by Yoshino et al. above, source (iv), on composites containing 20% multi-wall carbon nanotubes in a polymer matrix filled circle: alumina with 5.7% carbon black, generated by the inventors herein for comparison FIG. 1 demonstrates that the conductivity of the 15% single-wall carbon nanotube composite sintered by electric field-assisted sintering increases from 20.62 S/cm at −194° C. to 33.75 S/cm at 77° C. When combined with the high fracture resistance of these composites, these composites are superior to those of other reported carbon nanotube-containing ceramic composites where the carbon nanotubes produce either no increase in toughness of the ceramic or a only a marginal increase, the toughness limited by damage to the carbon nanotubes during high-temperature sintering.

To demonstrate that the composites of this invention have superior mechanical properties in addition their high electrical conductivity, the fracture toughnesses of the materials represented by the first two rows of Table I are shown in Table II.

TABLE II

Fracture Toughness of a Composite of the Present Invention vs. Alumina

| No. | Composition - additive(s) and volume %; matrix in parentheses | Processing Conditions | Relative Density (%) | Grain Size (nm) | Fracture Toughness (MPam$^{1/2}$) | Source |
|---|---|---|---|---|---|---|
| (1) | 0% (pure α-Al$_2$O$_3$) | SPS/1150° C./3 min | 100 | 349 | 3.3 | herein |
| (2) | SWCN: 5.7% (α-Al$_2$O$_3$) | SPS/1150° C./3 min | 100 | ~200 | 7.9 | herein |

Scanning electron microscopy, transmission electron microscopy, and high-resolution transmission electron microscopy indicated that the composites within the scope of the present invention consisted of a network of alumina grains with ropes of carbon nanotubes entangled with the grains. The result is a conductive material that is lightweight and resistant to corrosion and exhibits high strength and high toughness, rendering it unique in its usefulness in creating electrical circuitry in a wide range of applications.

The foregoing is offered primarily for purposes of illustration and explanation. Further variations, modifications and substitutions that, even though not disclosed herein, still fall within the scope of the invention may readily occur to those skilled in the art.

What is claimed is:

1. In an application requiring the conduction of an electric current as the result of a voltage applied between two terminals, the improvement comprising interposing between said terminals a composite material comprised of metal oxide and single-wall carbon nanotubes, said composite material having a density of at least 95% relative to a volume-averaged theoretical density, said composite material being the product of a process comprising consolidating a mixture of ceramic particles of less than 500 nm in diameter and single-wall carbon nanotubes into a continuous mass by compressing said mixture at a pressure of from about 10 MPa to about 200 MPa and a temperature of from about 800° C. to about 1,500° C. while passing a sintering pulsed direct electric current of from about 250 A/cm$^2$ to about 10,000 A/cm$^2$ through said mixture.

2. The improvement of claim 1 in which said density is at least 98% relative to said volume-averaged theoretical density.

3. The improvement of claim 1 in which said density is at least 99% relative to said volume-averaged theoretical density.

4. The improvement of claim 1 in which said metal oxide is a member selected from the group consisting of alumina, magnesium oxide, magnesia spinel, titania, cerium oxide, and zirconia.

5. The improvement of claim 1 in which said metal oxide is alumina.

6. The improvement of claim 1 in which said single-wall carbon nanotubes constitute from about 1% to about 50% of said composite.

7. The improvement of claim 1 in which said single-wall carbon nanotubes constitute from about 5% to about 25% of said composite.

8. The improvement of claim 1 in which said single-wall carbon nanotubes constitute from about 5% to about 20% of said composite.

9. The improvement of claim 1 in which said process comprises compressing said mixture at a pressure of from about 40 MPa to about 100 MPa and a temperature of from about 900° C. to about 1,400° C., and said sintering electric current is a pulsed direct current of from about 500 A/cm$^2$ to about 5,000 A/cm$^2$.

10. In an application requiring the conduction of an electric current as the result of a voltage applied between two terminals, the improvement comprising interposing between said terminals a composite material having a density of at least 95% relative to a volume-averaged theoretical density, said composite material being the product of a process comprising consolidating a mixture of alumina particles of less than 500 nm in diameter and single-wall carbon nanotubes into a continuous mass by compressing said mixture while passing a sintering electric current through said mixture, and in which said single-wall carbon nanotubes constitute from about 5% to about 25% of said composite.

11. The improvement of claim 10 in which said density is at least 98% relative to said volume-averaged theoretical density.

12. The improvement of claim 10 in which said density is at least 99% relative to said volume-averaged theoretical density.

13. The improvement of claim 12 in which said single-wall carbon nanotubes constitute from about 5% to about 20% of said composite.

* * * * *